(12) United States Patent
Narayan et al.

(10) Patent No.: US 10,654,879 B2
(45) Date of Patent: May 19, 2020

(54) NICKEL-BASED CATALYSTS FOR C=O REDUCTION AND OXYGEN EVOLUTION

(71) Applicant: UNIVERSITY OF SOUTHERN CALIFORNIA, Los Angeles, CA (US)

(72) Inventors: Sri Narayan, Arcadia, CA (US); Travis J. Williams, Los Angeles, CA (US); Zhiyao Lu, Duarte, CA (US); Debanjan Mitra, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 238 days.

(21) Appl. No.: 15/723,998

(22) Filed: Oct. 3, 2017

(65) Prior Publication Data

US 2018/0094012 A1    Apr. 5, 2018

Related U.S. Application Data

(60) Provisional application No. 62/403,419, filed on Oct. 3, 2016.

(51) Int. Cl.
| | |
|---|---|
| *C07F 15/04* | (2006.01) |
| *H01M 4/36* | (2006.01) |
| *C07C 29/157* | (2006.01) |
| *C07C 29/159* | (2006.01) |
| *C07C 29/147* | (2006.01) |

(52) U.S. Cl.
CPC ............ *C07F 15/04* (2013.01); *C07C 29/147* (2013.01); *C07C 29/157* (2013.01); *C07C 29/159* (2013.01); *C07F 15/045* (2013.01); *H01M 4/36* (2013.01)

(58) Field of Classification Search
None
See application file for complete search history.

(56) References Cited

PUBLICATIONS

Lu et al., ACS Catalysis, 2016, 6, pp. 6670-6673.*

* cited by examiner

*Primary Examiner* — Alicia L Otton
(74) *Attorney, Agent, or Firm* — Brooks Kushman P.C.

(57) ABSTRACT

A compound having formula I that is useful for C=O reduction is provided:

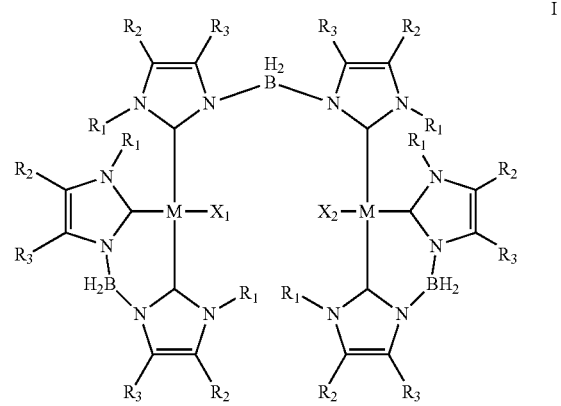

wherein:
M is a transition metal;
$X_1$, $X_2$ are each independently a counterion; and
$R_1$, $R_2$, $R_3$ are each independently H, $C_{1-6}$ alkyl, $C_{6-15}$ aryl, or $C_{6-15}$ heteroaryl.

20 Claims, 9 Drawing Sheets

Scheme 1

Scheme 2

Scheme 3

Fig. 9

NICKEL-BASED CATALYSTS FOR C=O REDUCTION AND OXYGEN EVOLUTION

CROSS-REFERENCE TO RELATED APPLICATIONS

This application claims the benefit of U.S. provisional application Ser. No. 62/403,419 filed Oct. 3, 2016, the disclosure of which is hereby incorporated in its entirety by reference herein.

STATEMENT REGARDING FEDERALLY SPONSORED RESEARCH OR DEVELOPMENT

The invention was made with Government support under Contract Nos. CHE-1566167 and CHE-1054910 awarded by the National Science Foundation. The Government has certain rights to the invention.

BACKGROUND

Figure 1:
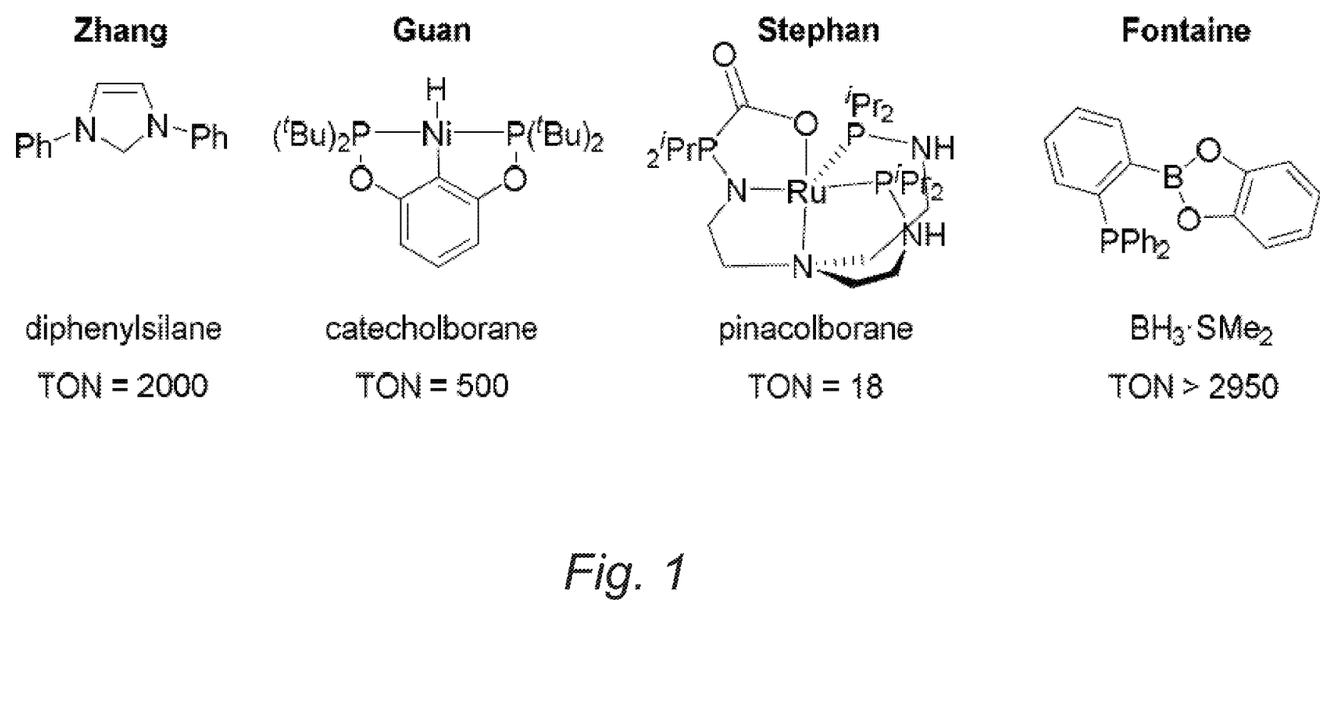
FIG. 1. Catalytic $CO_2$ Reduction with Silanes and Boranes. TONs are based on the number of hydrides delivered.
Figure 2:
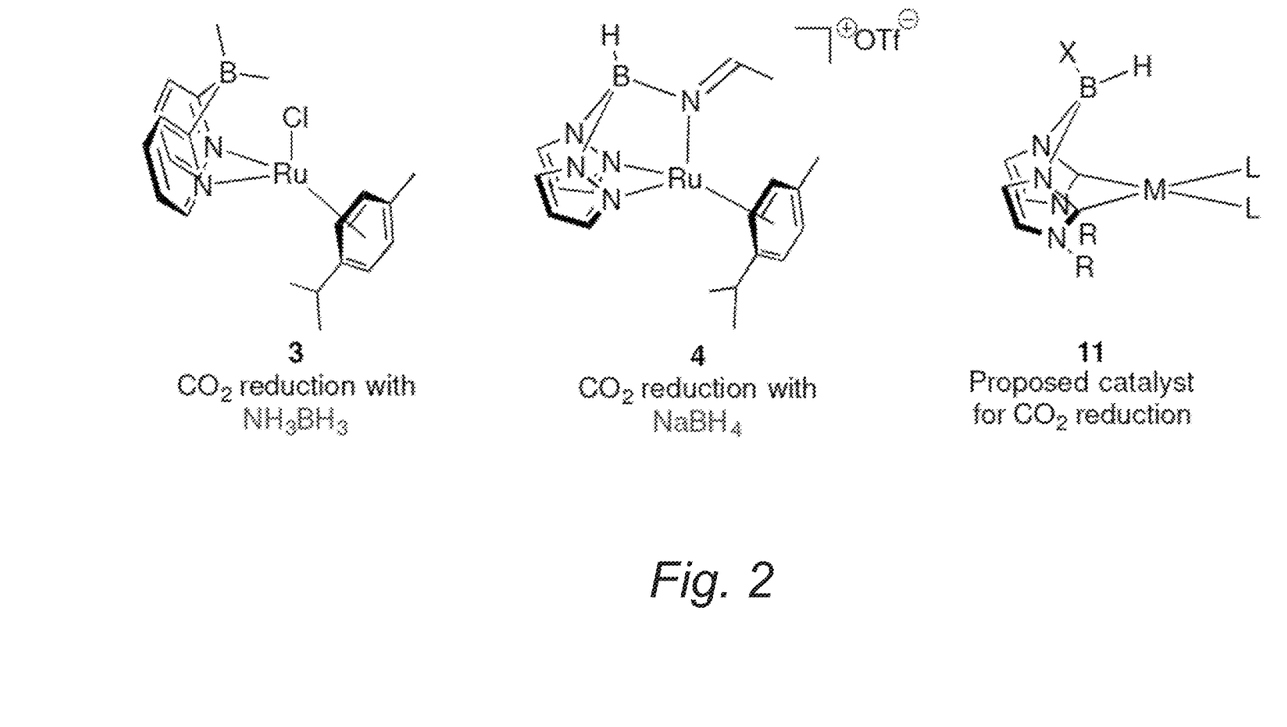
FIG. 2. Dual Center Catalytic Scaffolds for $CO_2$ Reduction.

The global atmospheric $CO_2$ concentration has recently (May 2015) passed the 400-ppm threshold for the first time on the NOAA record.[1] $CO_2$, a greenhouse gas, causes concerns about climate change and rising sea levels as its concentration escalates.[2] Among the options to transition from fossil fuel to more sustainable alternatives, solar fuel generated from $CO_2$ reduction is promising. Thus, effective $CO_2$ reduction is an important goal for the catalysis community.[3] Most $CO_2$ reduction products, such as methanol, formic acid, CO, etc., are useful C1 feedstocks in chemical synthesis; among them methanol has the highest volume energy density (and stored hydrogen density) at room temperature and is thus an outstanding product.[4] However, it is also a challenging target, because $CO_2$ is thermodynamically robust, so its activation requires a strong thermodynamic driving force.[5] Also, selective reduction of $CO_2$ is problematic; some known catalytic $CO_2$ reduction systems afford a mixture of products.[6] Regarding synthetic routes to methanol from $CO_2$, direct hydrogenation (with $H_2$) has been observed with a few ruthenium catalysts; these catalytic systems adopt forcing conditions or a multiple catalyst cascade and they have limited longevity.[7] Excellent and efficient non-renewable routes to methanol via syn gas are possible,3' 4 but room remains for improvement in renewable $CO_2$ to methanol conversion. Certain silanes or boranes can affect $CO_2$ reduction under much milder conditions.[8] For example, in FIG. 1 known, selective catalytic systems for $CO_2$ to methoxide reduction under low temperatures and pressures is shown. More recently, an example appeared wherein $BH_3$-THF reduces $CO_2$ to methoxide with $NaBH_4$ as the catalyst.[9] Although the catalysts in these systems are dramatically different, these low temperature $CO_2$ reductions have a common feature: they rely on silanes and boranes as reductants. The inexpensive and more easily handled $NaBH_4$ was only sparsely investigated for $CO_2$ reduction in the last century.[10] In 2015, Cummins and co-workers showed for the first time that $CO_2$ is reduced by $NaBH_4$ to triformatoborohydride, $HB(OCHO)_3^-$ in anhydrous acetonitrile.[11]

Accordingly, there is a need for improved inexpensive methods for converting $CO_2$ to methanol.

SUMMARY

The present invention solves one or more problems of the prior art by providing in at least one embodiment a catalyst for C=O reduction and oxygen evolution. The catalyst includes a compound having formula I:

wherein:

M is a transition metal;

$X_1$, $X_2$ are each independently a counterion; and $R_1$, $R_2$, $R_3$ are each independently H, alkyl, aryl, or heteroaryl.

In another embodiment, a catalyst for C=O reduction and oxygen evolution is provided. The catalyst includes a compound having formula II:

wherein:

$R_5$, $R_6$, $R_7$, $R_8$, $R_9$ are each independently H, $C_{1-6}$ alkyl, $C_{6-15}$ aryl, or $C_{6-15}$ heteroaryl; and M is a transition metal.

In still another embodiment, an electrochemically active substrate formed from compounds I and II set forth herein is provided. The electrochemically active substrate is formed from a method in which a metallic substrate is contacted with a compound having formulae I and II:

wherein:

M is a transition metal;

$X_1$, $X_2$ are each independently a counterion; and $R_1$, $R_2$, $R_3$ are each independently H, $C_{1-6}$ alkyl, $C_{6-15}$ aryl, or $C_{6-15}$ heteroaryl;

$R_5$, $R_6$, $R_7$, $R_8$, $R_9$ are each independently H, $C_{1-6}$ alkyl, $C_{6-15}$ aryl, or $C_{6-15}$ heteroaryl.

In yet another embodiment, a method for reducing carbon dioxide is provided. The method includes a step of contacting a compound having formula I or II set forth herein with carbon dioxide to form methanol.

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer) include alkyl, lower alkyl, $C_{1-6}$ alkyl, $C_{6-10}$ aryl, or $C_{6-10}$ heteroaryl; single letters (e.g., "n" or "o") are 1, 2, 3, 4, or 5; percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms are used herein, the presently disclosed and claimed subject matter can include the use of either of the other two terms.

As used herein, "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. The alkyl group can be optionally substituted (i.e., a "substituted alkyl") with another atom or functional group such as alkyl, substituted alkyl, halogen, aryl, substituted aryl, alkoxyl, hydroxyl, nitro, amino, alkylamino, dialkylamino, sulfate, mercapto, and the like.

As used herein, "aryl" means a monovalent aromatic hydrocarbon having a single ring (i.e., phenyl) or fused rings (i.e., naphthalene). In a refinement, such aryl groups include from 6 to 12 carbon ring atoms. In another refinement, such aryl groups include 6 to 10 carbon ring atoms. Representative aryl groups include, by way of example, phenyl biphenyl, naphthyl, anthranyl, and naphthalene-1-yl, naphthalene-2-yl, and the like. The term "arylene" means a divalent aryl group.

As used herein, "heteroaryl" means a monovalent aromatic group having a single ring or two fused rings and containing in the ring at least one heteroatom (typically 1 to 3 heteroatoms) selected from nitrogen, oxygen or sulfur. In a refinement, heteroaryl groups typically contain from 5 to 10 total ring atoms. In a refinement, heteroaryl groups have from 6 to 16 total ring atoms. In a refinement, the heteroaryl is a $C_{5-12}$ heteroaryl. Examples of heteroaryl include, but are not limited to, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. Additional examples heteroaryl groups include, but are not limited to, furanyl, thienyl, and pridinyl group. The term "heteroarylene" means a divalent heteroaryl group.

As used herein, "counterion" means the anionic counterion of an organic or inorganic acid neutralizing acid as described herein. The anionic counterion may be organic or inorganic. Examples of counterions include, but are not limited to, chloride, fluoride, bromide, iodide, toluenesulfonate, methanesulfonate, sulfate, phosphate, acetate, and the like.

ABBREVIATIONS

"MMO" means mixed metal oxide.
"TOF" means turnover frequency.
"TON" means turnover number.

In an embodiment, a compound having formula I which catalyzes the formation of methanol from carbon dioxide is provided:

I wherein:

M is a transition metal;

$X_1$, $X_2$ are each independently a counter-ion; and $R_1$, $R_2$, $R_3$ are each independently H, alkyl, aryl, or heteroaryl, and in particular, H, $C_{1-6}$ alkyl, $C_{6-15}$ aryl, or $C_{6-15}$ heteroaryl. In a variation, $X_1$ is a hydride or a borate group ($BH_2^-$) and $X_2$ is F, Cl, Br, I, tosylate, or mesylate. In a refinement, $R_1$, $R_2$, $R_3$ are each independently H. In a refinement, M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolinium, terbium, dysprosium, holmium, erbium, thallium, ytterbium, lutetium, hafnium, tantalum, tungsten, rhenium, osmium, iridium, gold, platinum, thallium, lead, bismuth, polonium, thorium, protactinium, uranium, neptunium, and plutonium. In another refinement, M is nickel.

In another embodiment, a compound having formula I which catalyzes the formation of methanol from carbon dioxide is provided:

II wherein:

$R_5$, $R_6$, $R_7$, $R_8$, $R_9$ are each independently H, alkyl, aryl, or heteroaryl, and in particular, H, $C_{1-6}$ alkyl, $C_{6-15}$ aryl, or $C_{6-15}$ heteroaryl. In a variation, $R_8$, $R_9$ are each independently H. In a refinement, the $R_5$ are each independently methyl or mesityl. In another refinement, $R_5$ are each independently methyl or mesityl. In a further refinement, $R_6$, $R_7$ are each independently H or methyl. M is a transition metal. In a refinement, M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolinium, terbium, dysprosium, holmium, erbium, thallium, ytterbium, lutetium, hafnium, tantalum, tungsten, rhenium, osmium, iridium, gold, platinum, thallium, lead, bismuth, polonium, thorium, protactinium, uranium, neptunium, and plutonium. In another refinement, M is nickel.

In another embodiment, an electrochemically active substrate formed by contacting a metallic substrate with any of the compounds of formulae I and II and all of its related variations and refinements is provided. In one refinement, the metallic substrate is nickel, and in particular, a nickel foam.

Figure 6:
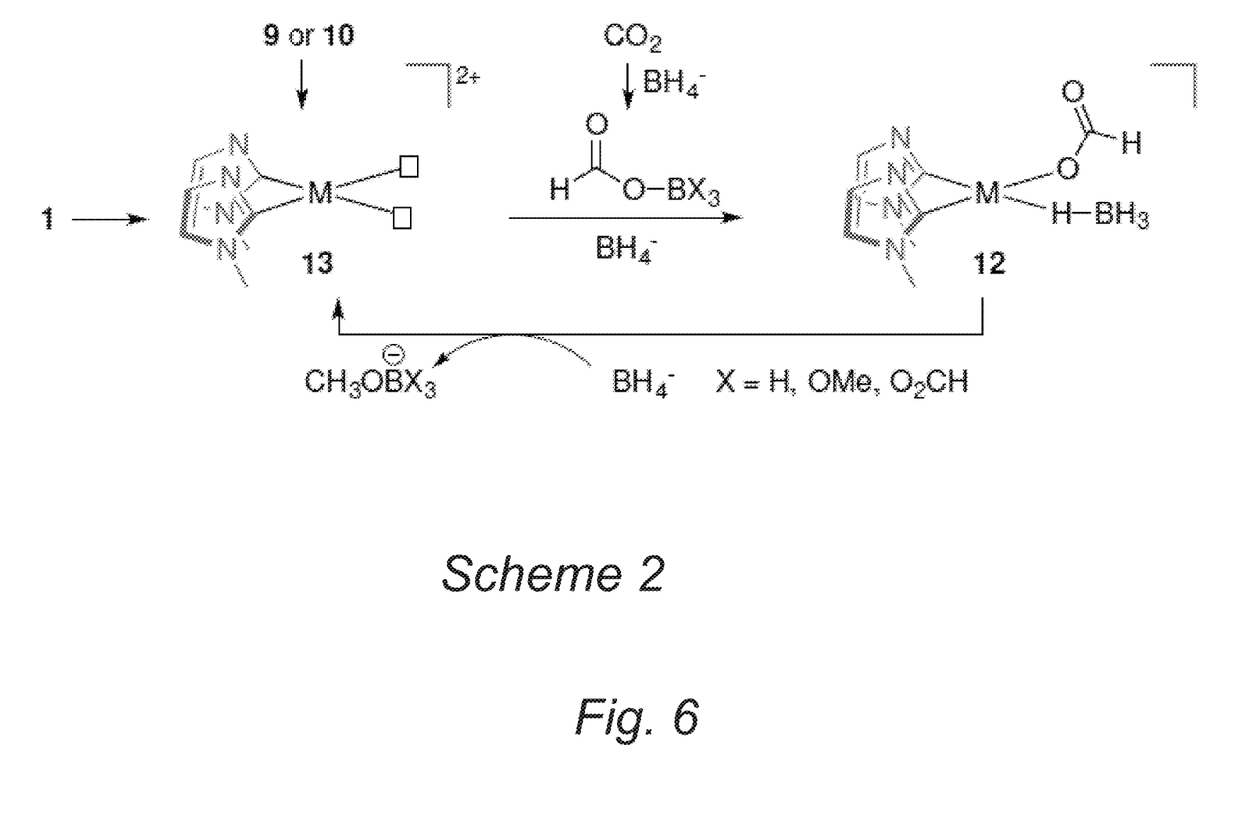
FIG. 6. Scheme 2. A plausible mechanism.

In another embodiment, a compound having formula III is provided (see FIG. 6):

III where $R_1$, $R_2$, $R_3$ and M are the same as set forth above.

In still another embodiment, a method for reducing carbon dioxide includes a step of contacting any of the compounds of formulae I and II and all of its related variations and refinements or the electrically active substrate with $CO_2$ to form methanol. Typically, this reaction occurs at a temperature from 20 to 80° C.

Figure 7:
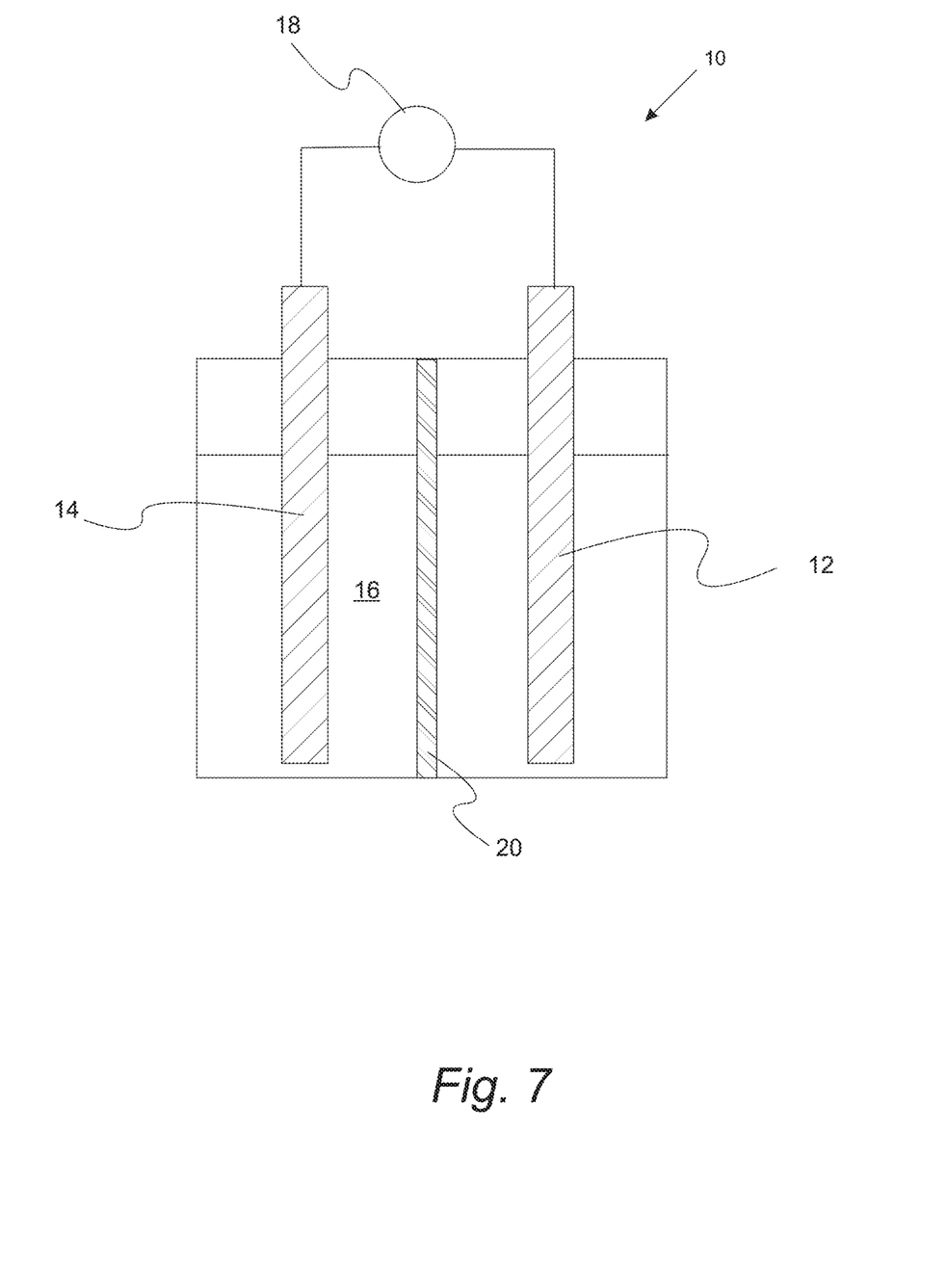
FIG. 7. Schematic of an electrochemical cell using the catalysts of the present invention.

With reference to FIG. 7, a schematic of an electrochemical cell using the compounds (i.e., catalysts) set forth above is provided. Electrochemical cell 10 includes electrochemically active substrate 12 and counter-electrode 14. Typically, electrochemical cell 10 further includes electrolyte 16 disposed between the electrochemically active substrate and the counter electrode. The electrochemical cell also includes voltage source 18 that applies a voltage across the electrochemical cell such that $O_2$ is converted to $H_2O$ when the electrochemically active substrate is contacted with $O_2$. Alternatively, voltage source 18 applies a voltage across the electrochemical cell such that $H_2O$ is converted to $O_2$ when the electrochemically active substrate is contacted with $H_2O$. In a refinement, electrochemical cell 10 includes a separator 20 (e.g., a battery separator).

Figure 3:
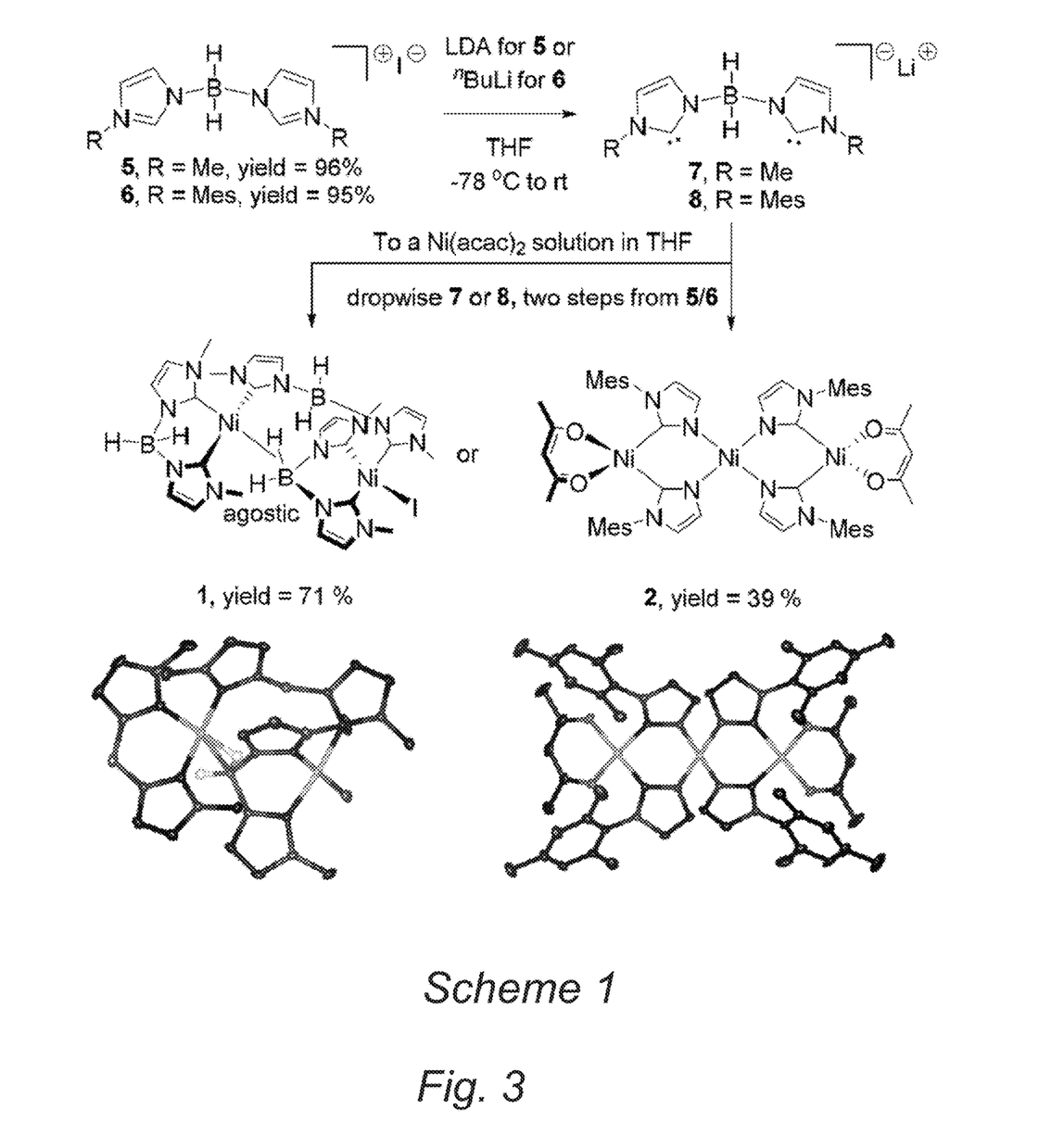
FIG. 3. Scheme 1. Syntheses and Structures of Nickel Compounds 1 and 2. Ellipsoids are drawn at the 50% probability level. Yields of 1 and 2 are based on the ligands.

In a variation, a method for catalytically converting $CO_2$ to methanol at room temperature by the compounds having formulae I and II and all of the related refinements and variation and in particular, by nickel catalysts 1 and 2. In particular, a new method for reduction of small molecule targets using dual site cooperative hydride delivery is provided.[12] For example, boron-ruthenium cooperation enables 4 as a nitrile reduction catalyst under mild conditions.[12e] Particularly, modest reactivity for $CO_2$ conversion to methoxide with catalysts 3 or 4 and $NaBH_4$ is observed (FIG. 3). It is presumed that these $CO_2$ reductions undergo dual-site cooperative hydride delivery. In order to improve catalytic reactivity, a family of Ni complexes supported by strongly donating bis(NHC)borate is designed and conceptually sketched as 11 in FIG. 3.

Accordingly, bis(imidazolium)borate monocations 5 and 6 (Scheme 1) featuring diverse steric environments was prepared. Cation 5 or 6 can be doubly de-protonated to form bis(imidazolium carbene)borate mono-anions, respectively 7 and 8, which can be treated with $Ni(acac)_2$ to form structurally novel nickel complexes 1 and 2 in preparatively useful yields over 2 steps. Formation of 1's nickel iodide bond results from persistence of the iodide counterion that accompanies 5.

Nickel(II) complexes 1 and 2 are bimetallic and trimetallic compounds, respectively (Scheme 1). In the solid-state structure of complex 1, one of three bidentate borate ligands bridges the two nickels. Another structural characteristic of 1 is that a B—H bond from one nickel's ligand interacts with another nickel in an agostic fashion. Quite unlike compound 1, compound 2 is free of all the boron atoms that are introduced in its synthesis. However, it retains the potential for dual site reactivity in that the three nickel atoms are held in close proximity by bridging imidizole groups. While not designed based on the enzymes, these multi-metallic structures are reminiscent of nickel-dependent hydrogenases that are reactive catalysts for $CO_2$ reduction under ambient conditions.[13]

Carbon Dioxide Reduction

Nickel(II) complexes 1 and 2 are bimetallic and trimetallic compounds, respectively (Scheme 1). In the solid-state structure of complex 1, one of three bidentate borate ligands bridges the two nickels. Another structural characteristic of 1 is that a B—H bond from one nickel's ligand interacts with another nickel in an agostic fashion. Quite unlike compound 1, compound 2 is free of all the boron atoms that are introduced in its synthesis. However, it retains the potential for dual site reactivity in that the three nickel atoms are held in close proximity by bridging imidizole groups. While not designed based on the enzymes, these multi-metallic structures are reminiscent of nickel-dependent hydrogenases that are reactive catalysts for $CO_2$ reduction under ambient conditions.[14]

Figure 4:
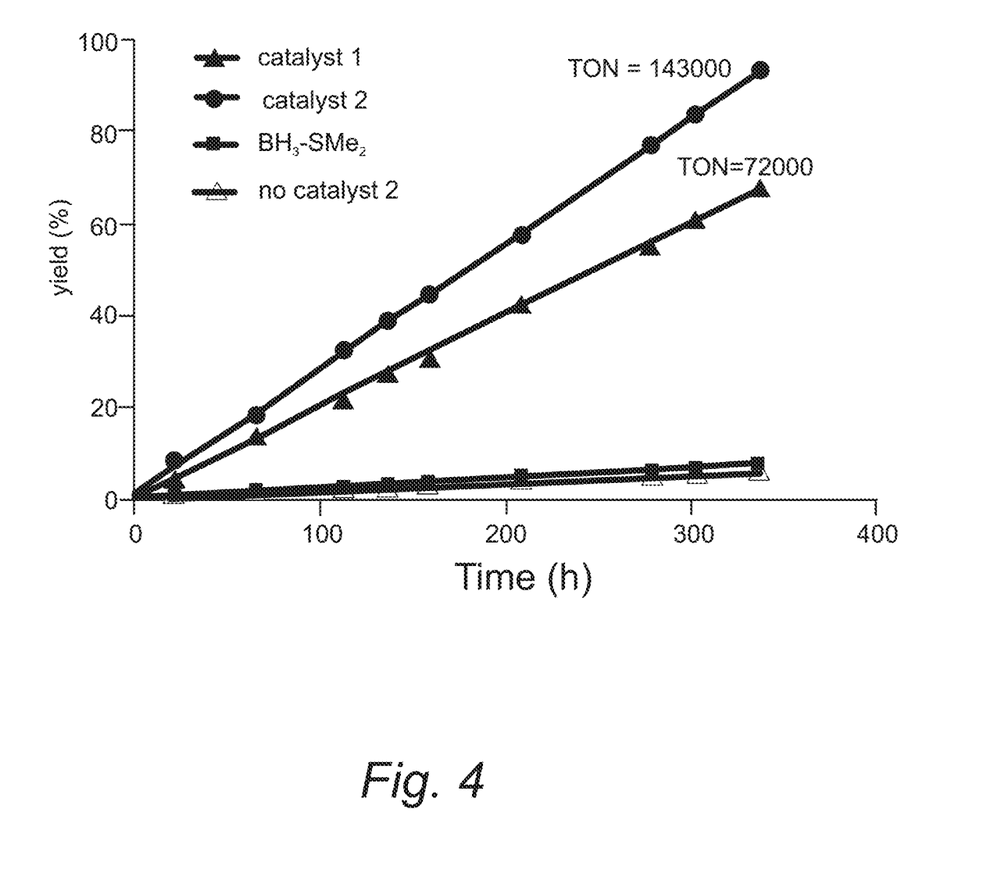
FIG. 4. Kinetic Profile of $CO_2$ Reduction by $NaBH_4$ Catalyzed by 1 and 2 in 2 Weeks. TONs are based on $CO_2$. Y-axis is yield of methanol based on $NaBH_4$. Loadings of Ni catalysts 1 and 2 and $BH_3.SMe_2$ are 1.9 µmol, 1.3 µmol, and 20 µmol, respectively.

Both 1 and 2 exhibit high reactivity as catalysts for room-temperature reduction of $CO_2$ by $NaBH_4$. For example, in two weeks, 1 and 2 can deliver more than 72000 or 143000 turnovers based on methanol product (TOFs are 6.7 $min^{-1}$ and 3.7 $min^{-1}$), respectively, without apparent loss of reactivity (FIG. 4). In a longevity experiment, catalyst 2 reached to a $CO_2$ TON of 1.1 million over 2 months (3.3 M TONs of hydride), and was still reactive when the reaction mixture was quenched. This TON is over three orders of magnitude more than the highest of $CO_2$ reduction by metal catalysts and a boron hydride in literature (FIG. 1).[8] Also noteworthy in this reaction is that >90% of the total hydride groups in $NaBH_4$ were converted to C—H bonds, which is far superior in productivity to a typical $NaBH_4$ reduction of a carbonyl group. The fate of boron containing species is clear: it affords sodium borate, which can be quantitatively crystalize from the mixture.

Nickel catalysts derived from 1 and 2 are exceptionally robust: they work in air and they have high tolerance for water. This feature allows $CO_2$ to be reduced in presence of a small amount of water to directly synthesize methanol. In a representative NMR experiment, in the presence of 1 vol % $H_2O$, the reaction yielded ca. 0.1 mmol methanol, instead of boron methoxides, with anestimated TON of 160 and TOF of 1.2 $min^{-1}$ (see supporting information).

Both nickel and the ligand are important to the mechanism (Table 1), because none of Ni(acac)$_2$, 5, or a mixture of Ni(acac)$_2$ with 5 or 6 or imidazole effect reduction. When 7 is used to affect the same transformation, stoichiometric conversion of formate to methoxide is observed. This reactivity is suspected to be enabled by nucleophilic activation of borohydride by the NHC.[15]

TABLE 1

Formate Conversion to Methoxides.

[HCOOX] $\xrightarrow[\text{25 min, rt}]{CD_3CN}$ [H$_3$COX]

| entry | catalyst | conversion | TON |
|---|---|---|---|
| 1 | 1 | 61% | 99 |
| 2 | 2 | 64% | 104 |
| 3 | Ni(acac)$_2$ | <5% | N/A |
| 4 | Ni(acac)$_2$ + methylimidazole | <5% | N/A |
| 5 | Ni(acac)$_2$ + 5 or 6 | <5% | N/A |
| 6 | 5 | <5% | N/A |
| 7[a,b] | 7 | 6.8% | 1[c] |
| 8[d] | 9 | 27% | 20 |

Conditions: formates are generated from the reaction between NaBH$_4$ (8.0 mg, 210 μmol) and HCO$_2$H (8.0 μL, 210 μmol) in CD$_3$CN (0.6 mL) in a J. Young tube. For the conversion of formates, catalyst (1.3 μmol) is added. Reaction progress is monitored by disappearance of formate peaks in $^1$H NMR. [a] CO$_2$ is used instead of FA to avoid protonation of 7. [b] The initial [formate] is 0.30 M. [c] TON is based on two carbenes per molecule of 7. [d] 2.6 μmol catalyst is added.

Kinetic studies were conducted on nickel complex 1. The CO$_2$ pressure was found to have little impact on the reduction: in parallel runs under different CO$_2$ pressures ranging from 15 to 45 psi, the same yield of methoxides is observed at different time points before completion. Complexes 1 and 2 are also effective catalysts for reduction of formic acid by NaBH$_4$ to methoxides. Sequential protonations of borohydride with formic acid give the same formates as those generated from CO$_2$: dissolving formic acid and NaBH$_4$ in acetonitrile affords identical $^1$H-NMR spectra. This enables formic acid as a convenient liquid surrogate for CO$_2$ for kinetic studies. The formate compounds are stable at room temperature and do not undergo further reduction until nickel catalyst 1 or 2 is introduced. Thereafter, methoxides form until all formates are consumed. This formate reduction is found to have first order dependence on [formate] and first order dependence on [1].

When 2 is treated with a stoichiometric amount of NaBH$_4$, rapid conversion of BH$_4^-$ to a new borane species and a new, broad hydride peak in $^1$H-NMR at δ($^1$H)=−13.8 ppm is observed, suggesting the formation of Ni—H species, which is consistent with a hydrogen bridging Ni and B.[8c] This Ni—H species, if charged with 1 atm CO$_2$, yields formate and methoxide peaks in $^1$H-NMR. Similarly, in an isotope labelling experiment, sodium formate-d$_1$ (DCOONa) was clearly reduced by this Ni—H system to a methoxide-d$_1$ product. These data show us that these conditions result in the formation of a nickel hydride intermediate that is capable of reduction of both CO$_2$ and the provided formate species. Although it is not known that it is a resting state, it is proposed that this is part of the proposed catalytic cycle.

Figure 5:
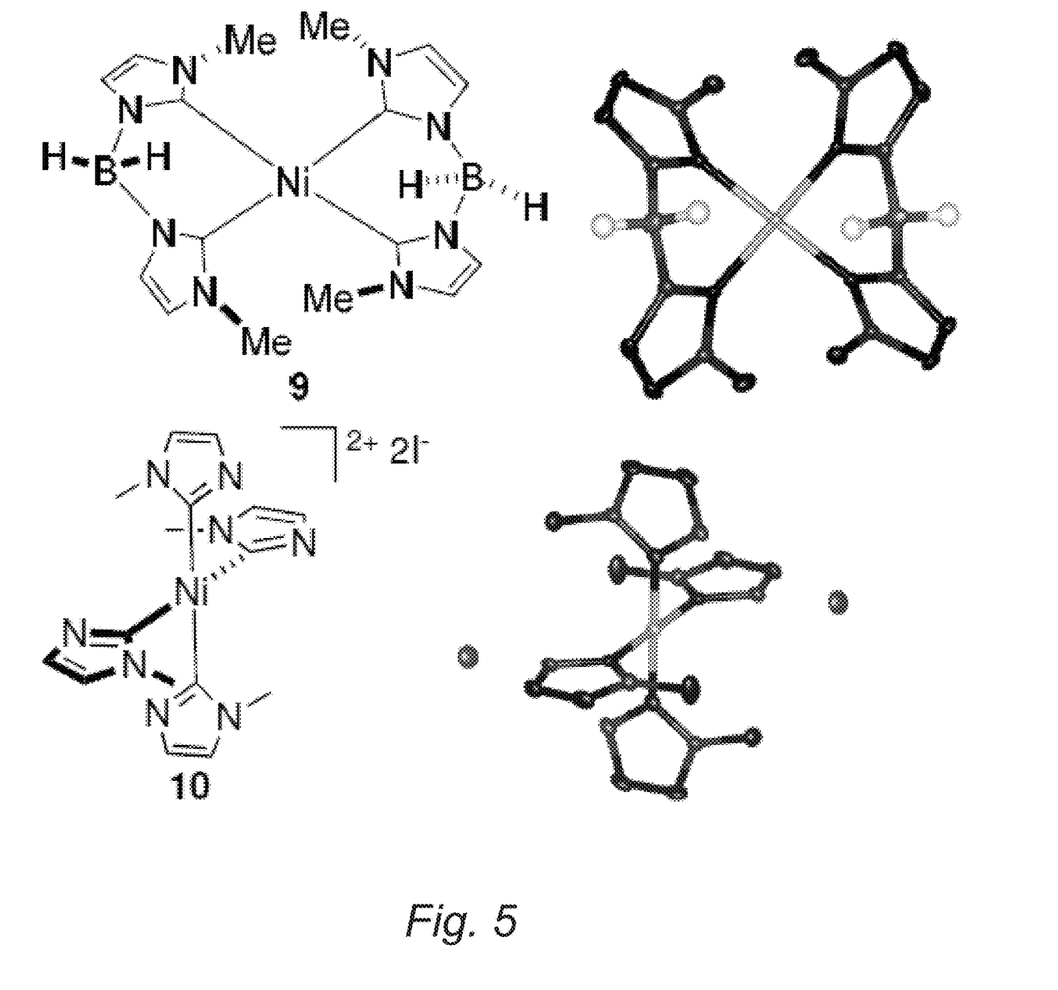
FIG. 5. Nickel Complexes 9, 10 and their Crystal Structures. ORTEP ellipsoids drawn at the 50% probability level.

Two nickel(II) species were isolated from the working reaction conditions, tetra(carbene) species 9 and 10 (FIG. 5). Complex 9 shows only modest reactivity in formate reduction: its reaction rate is ca. 5 times slower than 1, with only a modest TON (72) in 24 h being observed. Compound 10 is not long-lived: while crystallography data were obtained, it was not sufficiently robust to test in catalysis. It is suspected that the active catalyst is a monomeric nickel carbene complex with a reactive nickel hydride in its reducing form. This is based on the observation of first order kinetic dependence on [1], the isolations of 9 and 10, and the observation of a hydride in stoichiometric model reactions. It is proposed that dimer 1 cleaves to make the inert species 9 and a bis(carbene)nickel active species 13, which is reduced to give an active hydride (Scheme 2, FIG. 6). Although free ligands are not observed in the catalytic solution, it is suspected expect that 9 can slowly become 13, which then reduces formate using hydrides from BH$_4^-$ to 12. Alternatively, it might be possible that 10 is capable of CO$_2$ reduction through Ni, N dual site reactivity.

In conclusion, the synthesis and structural characterization of two novel NHC supported nickel complexes, 1 and 2 is provided herein. These nickel complexes can catalyze CO$_2$ reduction to methoxides with NaBH$_4$ under ambient conditions. The catalysts feature unprecedented stability, enabling a stunning >1 million turnovers. Ultimately, this system can be transitioned to H$_2$ as the reducing agent. Until then, the reaction features sodium borohydride, which has superior cost and convenience relative to more complex and sensitive borane and silane reagents. While work remains for the full understanding of the system's catalytic mechanism, preliminary data accommodate a single, probably mononuclear catalyst that enables rate-determining reduction of a boron formate.

Oxygen Evolution

It is further found that 1 of FIG. 4 is an efficient catalyst for electrocatalytic oxygen evolution from water: when a loading of 1 is solution-deposited onto a nickel foam substrate, the electrode effects O$_2$ evolution with an onset potential of ca.+0.55 V (versus MMO electrode, where the thermodynamic potential for O$_2$ evolution is +0.3 V) and current productivity of ca. 2× that of the bare nickel foam, a good catalyst for this reaction in its own right. It is believed that this most likely involves transformation of precursor 1 into a heterogeneous active species that is potentially generally useful for electrooxidation.

Figure 8A:
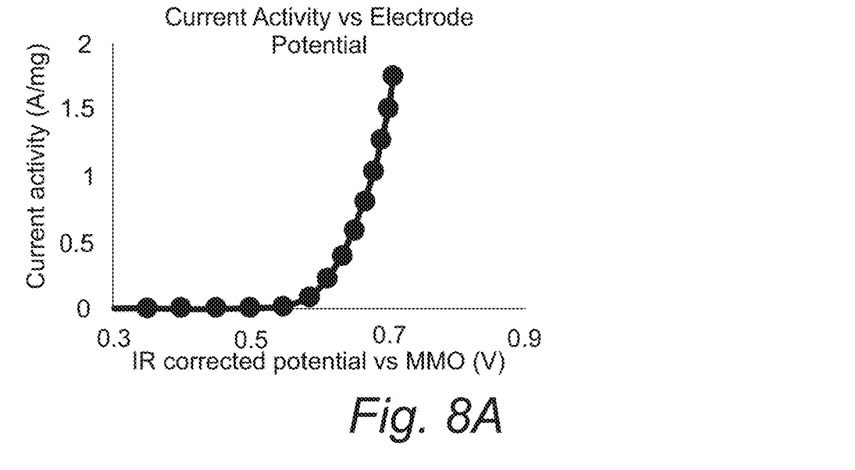
FIGS. 8A, 8B, and 8C. Oxygen Evolution from Nickel Complex 1. (A) IR corrected potential vs. MMO. (B) IR corrected potential vs. time. (C) Tafel Slope.
Figure 8B:
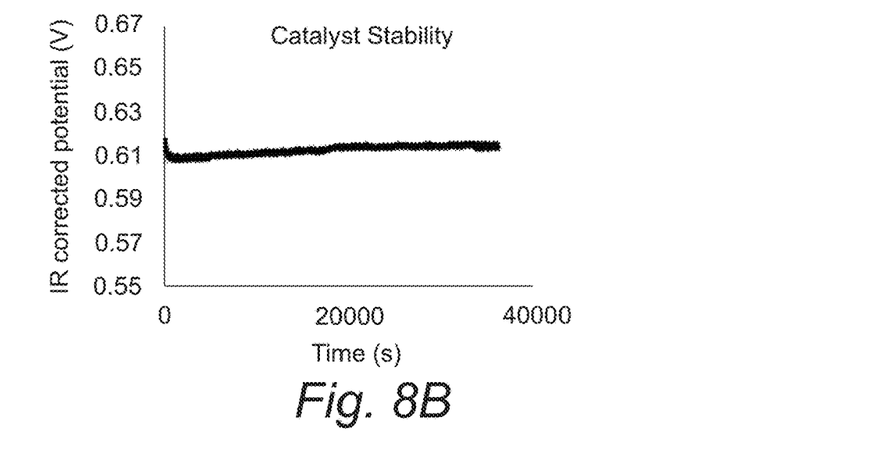
Figure 8C:
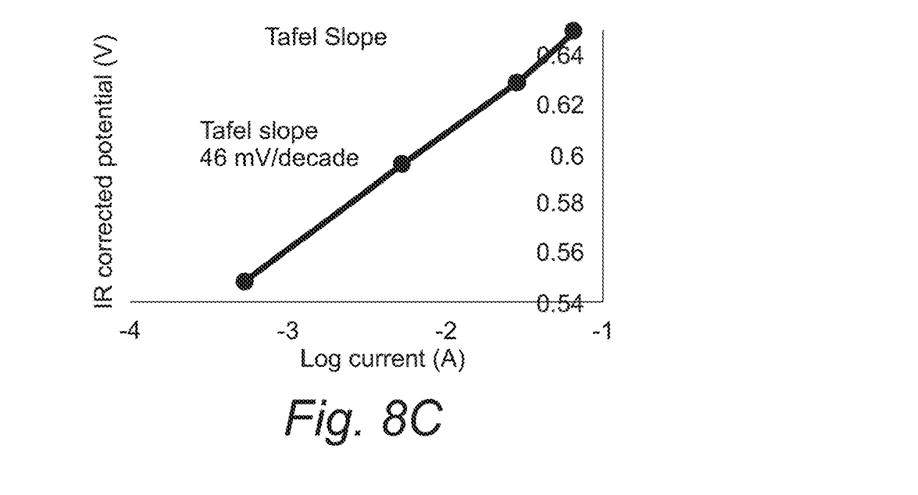

FIG. 8 shows unoptimized, preliminary data for O$_2$ evolution from an embodiment of a catalyst. A catalyst comprised of 300 μg of nickel species 1 was assembled, which was solution-deposited onto 1 cm$^2$ of a nickel foam wafer. The resulting electrode was used in the oxygen evolution reaction with potential calibrated to a MMO electrode (Hg/HgO: thermodynamic potential for O$_2$ evolution=+0.3 V).

FIG. 8A shows oxygen evolution at an overpotential of ca.+0.25 V, which can be taken as an excellent starting point for low overpotential catalysis. FIG. 8B shows the stability of the proposed catalyst over 10 hours. This was a critical and highly unexpected finding: it shows that while the borate groups that tether the catalyst's carbene moieties cannot possibly be stable under the reaction conditions, precursor 1 converts to an active catalyst that is long-lived. A Tafel plot was also recorded (FIG. 8C), which shows a slope of 46 mV/decade at low overpotential. This value of Tafel slope is consistent with Ni$^{II}$/Ni$^{III}$ cycle, which matches expectations based on the oxidation state of the precursor.

Figure 9:
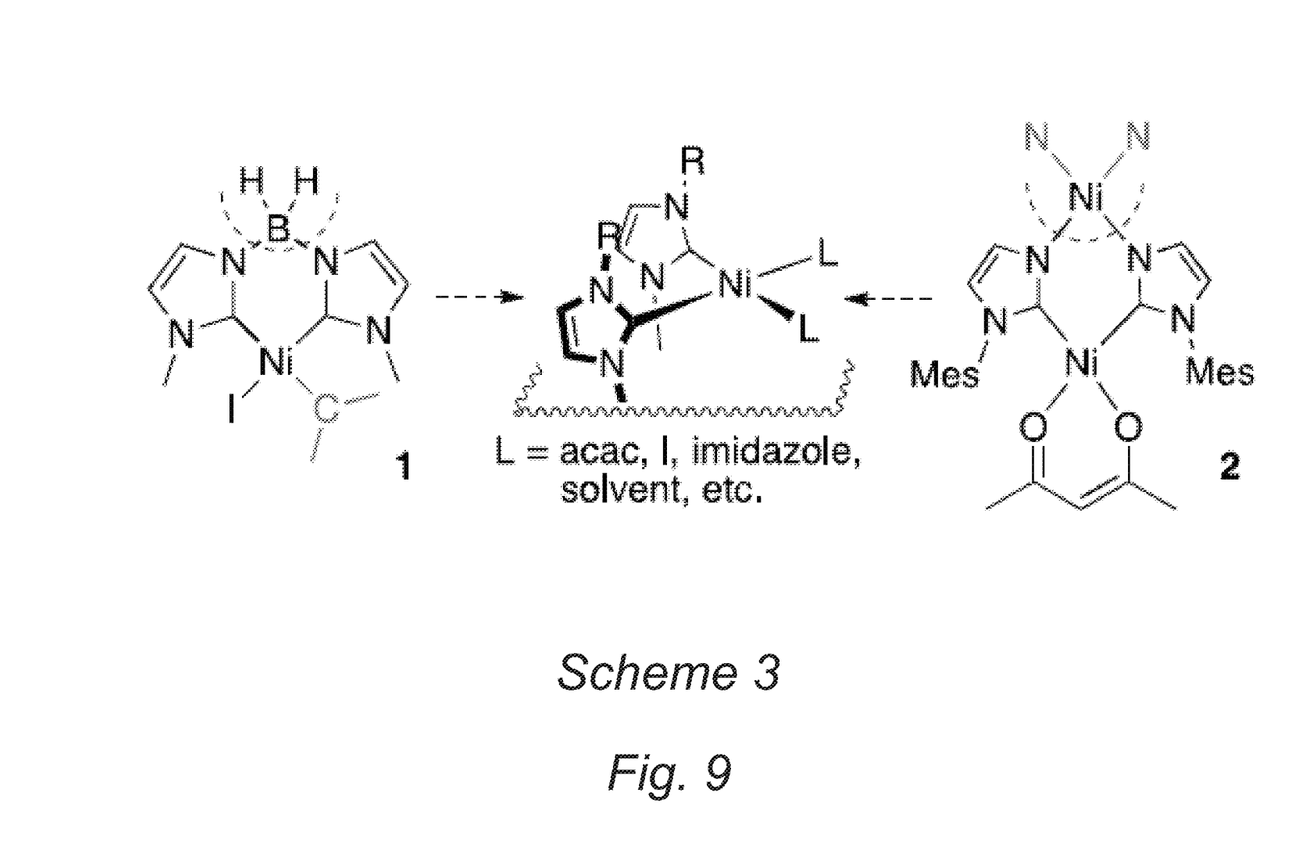
FIG. 9. Scheme 3 showing proposed Mounting of 1 and 2.

Electrode Characterization Experiments. The active catalyst is proposed to be formed by cleaving the linking group between the imidazolium carbene groups of 1 or 2 and using the free imidazole nitrogen atoms as covalent handles to anchor the catalyst to the heterogeneous surface (FIG. 9, Scheme 3). XPS data on a 1-functionalized nickel foam surface is consistent with the presence of imidazole, nickel (II), and an oxidized iodine species. Boron is not cleanly detected, as if it is absent.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

[1] Dlugokencky, E.; Tans, P. Trends in Atmospheric Carbon Dioxide, NOAA/ESRL, www.esri.noaa.gov/gmd/ccgg/trends/

[2] (a) Arakawa, H.; Aresta, M.; Armor, J. N.; Barteau, M. A.; Beckman, E. J.; Bell, A. T.; Bercaw, J. E.; Creutz, C.; Dinjus, E.; Dixon, D. A.; Domen, K.; DuBois, D. L.; Eckert, J.; Fujita, E.; Gibson, D. H.; Goddard, W. A.; Goodman, D. W.; Keller, J.; Kubas, G. J.; Kung, H. H.; Lyons, J. E.; Manzer, L. E.; Marks, T. J.; Morokuma, K.; Nicholas, K. M.; Periana, R.; Que, L.; Rostrup-Nielson, J.; Sachtler, W. M. H.; Schmidt, L. D.; Sen, A.; Somorjai, G. A.; Stair, P. C.; Stults, B. R.; Tumas, W. *Chem. Rev.* 2001, 101, 953-996; (b) Lewis, N. S.; Nocera, D. G. *Proc. Natl. Acad. Sci. U.S.A* 2006, 103, 15729-15735; (c) Aresta, M.; Dibenedetto, A. *Dalton Trans.* 2007, 2975-2992; (d) Aresta, M.; Dibenedetto, A.; Angelini, A. *Chem. Rev.* 2014, 114, 1709-1742.

[3] Appel, A. M.; Bercaw, J. E.; Bocarsly, A. B.; Dobbek, H.; DuBois, D. L.; Dupuis, M.; Ferry, J. G.; Fujita, E.; Hille, R.; Kenis, P. J. A.; Kerfeld, C. A.; Morris, R. H.; Peden, C. H. F.; Portis, A. R.; Ragsdale, S. W.; Rauchfuss, T. B.; Reek, J. N. H.; Seefeldt, L. C.; Thauer, R. K.; Waldrop, G. L. *Chem. Rev.* 2013, 113, 6621-6658; (b) Tanaka, R.; Yamashita, M.; Nozaki, K. *J. Am. Chem. Soc.* 2009, 131, 14168-14169; Schmeier, T. J.; Dobereiner, G. E.; Crabtree, R. H; Hazari, N. *J. Am. Chem. Soc.* 2011, 133, 9274-9277.

[4] (a) Olah, G. A. *Angew. Chem. Int. Ed.,* 2005, 44, 2636-2639; (b) Olah G. A. *Chem. Eng. New,* 2003, 81, 5; (c) Olah, G. A.; Prakash, S. G. K.; Goeppert A. *J. Org. Chem.* 2009, 74, 487-498. (d) Olah, G. A.; Goeppert, A.; Prakash, G. K. S. Beyond Oil and Gas: The Methanol Economy, Wiley-VCH, 2006.

[5] (a) Wang, J. L.; Miao, C. X.; Dou, X. Y.; Gao, J.; He, L. N. *Curr. Org. Chem.* 2011, 15, 621-646; (b) Cuéllar-Franca, R. M.; Azapagic, A. *J. CO$_2$ Util.* 2015, 9, 82-102.)

[6] For a representative example, see Schäfer, A.; Saak, W.; Haase, D.; Müller, T. *Angew. Chem., Int. Ed.* 2012, 51, 2981-2984.

[7] (a) Wesselbaum, S.; vom Stein, T.; Klankermayer, J.; Leitner, W. *Angew. Chem. Int. Ed.* 2012, 51, 7499-7502; (b) Huff, C. A.; Sanford, M. S. *J. Am. Chem. Soc.* 2011, 133, 18122-18125; Rezayee, N. M.; Huff, C. A.; (c) Sanford M. S. *J. Am. Chem. Soc.* 2015, 137, 1028-1031; (d) Kothandaraman, J.; Goeppert, A.; Czaun, M.; Olah, G.; Prakash, G. K. S. *J. Am. Chem. Soc.* 2016, 138, 778-781.

[8] (a) Riduan, S. N.; Zhang, Y.; Ying, J. Y. *Angew. Chem. Int. Ed.* 2009, 48, 3322-3325; (b) Ashley, A. E.; Thompson, A. L.; O'Hare, D. *Angew. Chem. Int. Ed.* 2009, 48, 9839-9843; (c) Chakraborty, S.; Zhang, J.; Krause, J. A.; Guan, H. *J. Am. Chem. Soc.* 2010, 132, 8872-8873; (d) Sgro, M. J.; Stephan, D. W. *Angew. Chem. Int. Ed.* 2012, 51, 11343-11345; (e) Berkefeld, A.; Piers, W. E.; Parvez, M.; Castro, L.; Maron, L.; Eisenstein, O. *Chem. Sci.* 2013, 4, 2152-2162; (f) Courtemanche, M.-A.; Légaré, M.-A.; Maron, L.; Fontaine, F.-G. *J. Am. Chem. Soc.* 2013, 135, 9326-9329.

[9] (a) Fujiwara, K.; Yasuda, S.; Mizuta, T. *Organometallics* 2014, 33, 6692-6695; (b) Légaré, M.-A.; Courtemanche. M.-A.; Fontaine, F.-G. *Chem. Commun.* 2014, 50, 11362-11365.

[10] (a) Wartik, T.; Pearson, R. K. *J. Am. Chem. Soc.* 1955, 77, 1075; (b) Wartik, T.; Pearson, R. K. *J. Inorg. Nucl. Chem.* 1958, 7, 404-411; (c) Pearson, R. K.; Wartik, T. U.S. Pat. No. 2,872,474, 1959; (d) Burr, J. G., Jr.; Brown, W. G.; Heller, H. E. *J. Am. Chem. Soc.* 1950, 72, 2560-2562; (e) Schmidbaur, H.; Weib, E.; Muller, G. *Synth. React. Inorg. Met. Chem.* 1985, 15, 401-413; (f) Eisenberg, F., Jr.; Bolden, A. H. *Carbohydr. Res.* 1967, 5, 349-350. (g) Yi, C. S.; Liu, N. *Organometallics* 1995, 14, 2616-2617.

[11] Knopf, I.; Cummins C. C. *Organometallics* 2015, 34, 1601-1603.

[12] (a) Conley, B. L., Williams, T. J. *Chem. Commun.* 2010, 46, 4815-4817. (b) Conley, B. L., Guess, D., Williams, T. J. *J. Am. Chem. Soc.* 2011, 133, 14212-14215. (c) Lu, Z., Conley, B. L., Williams, T. J. *Organometallics,* 2012, 31, 6705-6714. (d) Lu, Z., Malinoski, B., Flores, A. V., Guess, D., Conley, B., Williams, T. J. *Catalysts* 2012, 2, 412-421. (e) Lu, Z., Williams, T. J. *J. Chem. Commun.* 2014, 50, 5391-5393.

[13] Volbeda, A.; Charon, M.-H.; Piras, C.; Hatchikian, E. C.; Frey, M.; Fontecilla-Camps, J. C. *Nature,* 1995, 373, 580-587.

[14] Volbeda, A.; Charon, M.-H.; Piras, C.; Hatchikian, E. C.; Frey, M.; Fontecilla-Camps, J. C. *Nature,* 1995, 373, 580-587.

[15] (a) Huang, F.; Lu, G.; Zhao, L.; Li, H.; Wang, Z.-X. *J. Am. Chem. Soc.* 2010, 132, 12388-12396; (b) Duong, H. A.; Tekavec, T. N.; Arif, A. M.; Louie, J. *Chem. Commun.* 2004, 112-113; (c) Kayaki, Y.; Yamamoto, M.; Ikariya, T. *Angew. Chem. Int. Ed.* 2009, 48, 4194-4197.

What is claimed is:

1. A compound having formula I:

wherein:

M is a transition metal;

$X_1$, $X_2$ are each independently a counterion; and $R_1$, $R_2$, $R_3$ are each independently H, $C_{1-6}$ alkyl, $C_{6-15}$ aryl, or $C_{6-15}$ heteroaryl.

2. The compound of claim 1 wherein M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolinium, terbium, dysprosium, holmium, erbium, thallium, ytterbium, lutetium, hafnium, tantalum, tungsten, rhenium, osmium, iridium, gold, platinum, thallium, lead, bismuth, polonium, thorium, protactinium, uranium, neptunium, and plutonium.

3. The compound of claim 1 wherein M is nickel.

4. The compound of claim 1 wherein $X_1$ is a hydride or a borate group ($BH_2^-$) and $X_2$ is F, Cl, Br, I, tosylate, or mesylate.

5. The compound of claim 1 wherein $R_1$, $R_2$, $R_3$ are each independently H.

6. A compound having formula II:

II wherein:

$R_5$, $R_6$, $R_7$, $R_8$, $R_9$ are each independently H, $C_{1-6}$ alkyl, $C_{6-15}$ aryl, or $C_{6-15}$ heteroaryl; and M is a transition metal.

7. The compound of claim 6 wherein M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolinium, terbium, dysprosium, holmium, erbium, thallium, ytterbium, lutetium, hafnium, tantalum, tungsten, rhenium, osmium, iridium, gold, platinum, thallium, lead, bismuth, polonium, thorium, protactinium, uranium, neptunium, and plutonium.

8. The compound of claim 6 wherein M is nickel.

9. The compound of claim 6 wherein $R_8$, $R_9$ are each independently H.

10. The compound of claim 6 wherein $R_5$ are each independently methyl or mesityl.

11. The compound of claim 6 wherein $R_5$ are each independently methyl or mesityl.

12. The compound of claim 6 wherein $R_6$, $R_7$ are each independently H or methyl.

13. An electrochemically active substrate formed by a method comprising: contacting a metallic substrate with a compound having formula I or II:

I

II wherein:

M is a transition metal;

$X_1$, $X_2$ are each independently a counterion; and $R_1$, $R_2$, $R_3$ are each independently H, $C_{1-6}$ alkyl, $C_{6-15}$ aryl, or $C_{6-15}$ heteroaryl;

$R_5$, $R_6$, $R_7$, $R_8$, $R_9$ are each independently H, $C_{1-6}$ alkyl, $C_{6-15}$ aryl, or $C_{6-15}$ heteroaryl.

14. The electrochemically active substrate of claim 13 wherein the metallic substrate includes nickel.

15. An electrochemical cell comprising the electrochemically active substrate of claim 13 and a counter-electrode.

16. The electrochemical cell of claim 15 further comprising an electrolyte disposed between the electrochemically active substrate and the counter-electrode.

17. The electrochemical cell of claim 16 further comprising a voltage source that applies a voltage across the electrochemical cell such that $O_2$ is converted to $H_2O$ when the electrochemically active substrate is contacted with $O_2$.

18. The electrochemical cell of claim 17 further comprising a voltage source that applies a voltage across the electrochemical cell such that $H_2O$ is converted to $O_2$ when the electrochemically active substrate is contacted with $H_2O$.

19. A method comprising: contacting a compound having formula I or II with carbon dioxide to form methanol:

I

II wherein:

M is a transition metal;

$X_1$, $X_2$ are each independently a counterion; and $R_1$, $R_2$, $R_3$ are each independently H, $C_{1-6}$ alkyl, $C_{6-15}$ aryl, or $C_{6-15}$ heteroaryl;

$R_5$, $R_6$, $R_7$, $R_8$, $R_9$ are each independently H, $C_{1-6}$ alkyl, $C_{6-15}$ aryl, or $C_{6-15}$ heteroaryl.

20. A compound having formula III:

III wherein:

M is a transition metal; and $R_1$, $R_2$, $R_3$ are each independently H, $C_{1-6}$ alkyl, $C_{6-15}$ aryl, or $C_{6-15}$ heteroaryl.

* * * * *